(12) United States Patent
Krumme

(10) Patent No.: US 8,299,670 B2
(45) Date of Patent: Oct. 30, 2012

(54) CT SCANNER GANTRY WITH AEROSTATIC BEARING AND SEGMENTED RING MOTOR

(75) Inventor: Nils Krumme, Feldafing (DE)

(73) Assignee: Schleifring und Apparatebau GmbH, Fürstenfeldbruck (DE)

( * ) Notice: Subject to any disclaimer, the term of this patent is extended or adjusted under 35 U.S.C. 154(b) by 425 days.

(21) Appl. No.: 12/538,684

(22) Filed: Aug. 10, 2009

(65) Prior Publication Data

US 2010/0034492 A1    Feb. 11, 2010

(30) Foreign Application Priority Data

Aug. 11, 2008  (DE) .......................... 10 2008 041 151

(51) Int. Cl.
*H02K 5/16* (2006.01)

(52) U.S. Cl. ....................................................... 310/90

(58) Field of Classification Search .................... 310/90, 310/90.5; 384/107, 109
See application file for complete search history.

(56) References Cited

U.S. PATENT DOCUMENTS

| | | | |
|---|---|---|---|
| 3,586,435 A * | 6/1971 | Del Carlo et al. | 384/100 |
| 4,032,199 A * | 6/1977 | Jenness | 384/310 |
| 5,355,040 A * | 10/1994 | New | 310/90.5 |
| 6,344,703 B1 * | 2/2002 | Sawada et al. | 310/90 |
| 6,404,845 B1 | 6/2002 | Sharpless et al. | |
| 7,477,721 B2 | 1/2009 | Chappo et al. | |

FOREIGN PATENT DOCUMENTS

WO    2008017498    2/2008

* cited by examiner

*Primary Examiner* — Dang Le

(74) *Attorney, Agent, or Firm* — Meyertons, Hood, Kivlin, Kowert & Goetzel, P.C.; Eric B. Meyertons

(57) ABSTRACT

Disclosed is a device having a rotor that is adapted to be rotated relative to a stator, with hydrostatic bearings being used as radial bearings and as axial bearings of the rotor. A motor is provided as a direct drive, having a ring-shaped part and also a plurality of motor segments which are in magnetic engagement with the ring-shaped part. In order to generate additional bearing load force, additional motor segments having permanent magnets are provided. For reasons of safety, axial support rolls are provided which, when the motor has attained a given bearing load force, are spaced from a running face of the rotor, and which, in a case of too low or an absence of load force, prevent a displacement of the rotor away from the axial bearings.

5 Claims, 5 Drawing Sheets

FIG 2 A-A

CT SCANNER GANTRY WITH AEROSTATIC BEARING AND SEGMENTED RING MOTOR

CROSS-REFERENCE TO RELATED APPLICATIONS

This application claims priority from pending German application 10 2008 041 151.5 filed on Aug. 11, 2008.

BACKGROUND OF THE INVENTION

1. Field of the Invention

The invention relates to a rotatable device having an aerostatic bearing and also a direct drive in the form of a segmented ring motor. Devices of this kind are preferably used as rotors in computer tomographs (CT scanners).

2. Description of the Relevant Art

In computer tomographs an X-ray tube rotates together with a detector disposed opposite to it around the body of a patient. The X-ray tube and the detector are mounted to the rotating part of a gantry, with the rotating part being supported to be rotatable relative to a stationary part. In modern computer tomographs of high resolution, the rotating part of the gantry rotates at high rotation numbers, for example 300 r.p.m. Simultaneously a very high positional tolerance of the gantry in ranges distinctly below 1 mm is required. With this, mechanical bearings frequently approach limits of what is technologically possible. Here, an elegant way of providing a bearing function is by means of an aerodynamic bearing, also known as an air bearing.

U.S. Pat. No. 6,404,845 B1 discloses a gantry of a computer tomograph having an aerodynamic bearing. In this, a rotating part of the gantry is held in a desired position by axially and radially disposed bearings. Here it is difficult to control the function of an axial bearing. This consists of two bearings disposed opposite to each other on opposite sides of the rotating body of the gantry. A problem with this is that smallest of changes of the configuration of the rotating body, in particular of a distance between the locations of support of the oppositely disposed axial air bearings directly affect the bearing clearance and therewith the bearing properties.

A further improvement of this arrangement is disclosed in WO 2008/017498 A2. This document describes a bearing arrangement in which at least one of the axial bearings can be moved along an axial direction towards its bearing basis, in order to compensate these fluctuations of thickness of the rotating body.

SUMMARY OF THE INVENTION

Embodiments disclosed herein are based on the object of further developing a rotatable device having aerostatic bearing facilities and a direct drive in the form of a segmented ring motor so that it can be equipped with a simpler and thus also less costly bearing means. Embodiments disclosed herein may also improve the emergency running properties of rotatable devices having aerostatic bearing means, such as CT scanners.

According to an embodiment a rotatable device includes: a rotor; a stator, with the rotor being supported to be rotatable relative to the stator; at least one hydrostatic bearing serving as a radial bearing of the rotor; at least one hydrostatic bearing serving as an axial bearing of the rotor; and a direct drive motor including a ring-shaped part and also at least one motor segment which is in magnetic engagement with the ring-shaped part of the motor to generate a torque; wherein at least one further motor segment is provided for generating exclusively a load force of the rotor on the axial hydrostatic bearings.

An achievement of another of the above objects is provided by a rotatable device including: a rotor; a stator, with the rotor being supported to be rotatable relative to the stator; at least one hydrostatic bearing serving as a radial bearing of the rotor; and at least one hydrostatic bearing serving as an axial bearing of the rotor; wherein at least one hydrostatic bearing includes a bearing surface of a synthetic material, and at least one bearing pad of aluminum. As an alternative, at least one hydrostatic bearing includes a bearing surface of aluminum, and at least one bearing pad of sintered graphite.

BRIEF DESCRIPTION OF THE DRAWINGS

In the following the invention will be described by way of example, without limitation of the general inventive concept, on examples of embodiment and with reference to the drawings.

Figure 1:
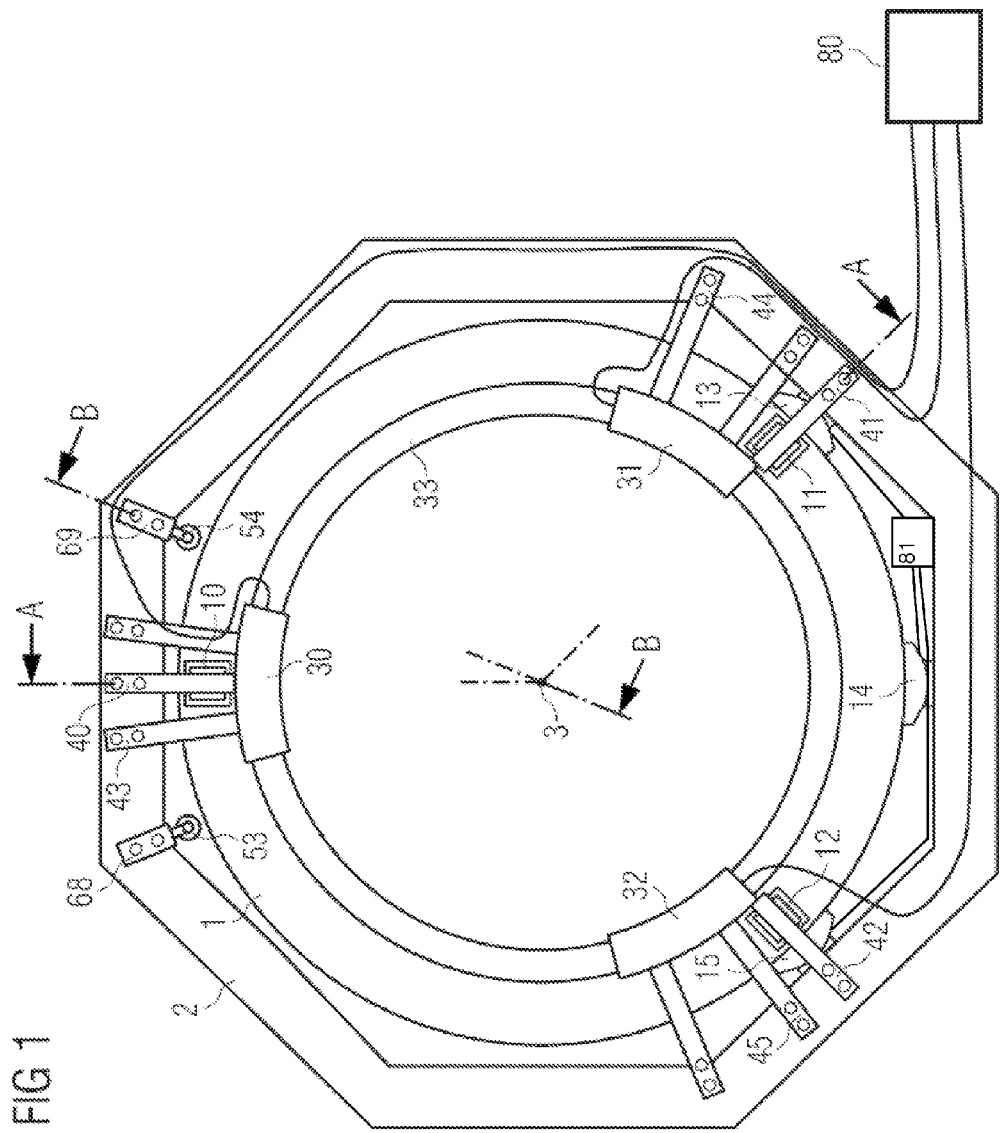
FIG. 1 shows a first device from a front side.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE DRAWINGS

FIG. 1 shows a first device from the front side. A rotor 1 is disposed within a stator 2 and is supported along a radial direction by air bearings 13, 14 and 15 to be rotatable about an axis 3. For driving the rotor relative to the stator and for generating an axial load force in axial air bearings 10, 11 and 12, a motor is provided in the form of a direct drive. This direct drive includes a ring-shaped part 33 which is firmly connected to the rotor 1 of the device. Motor segments 30, 31 and 32 are in engagement with this ring-shaped part. These motor segments are supplied with current by a control unit in such manner that they generate a magnetic field which on the one hand sets the ring-shaped part 33 of the motor into a rotational movement, and on the other hand draws it along a direction out of the plane of the illustration, so that the rotor 1 is urged against the axial air bearings 10, 11 and 12. The motor segments 30, 31 and 32 are attached to the stator 2 by means of supports 43, 44 and 45. Similarly, the axial air bearings 10, 11 and 12 are attached to the stator 2 by means of supports 40, 41 and 42. The current supply and control of the motor segments 30, 31 and 32 is effected via the motor control means 80.

Figure 2:
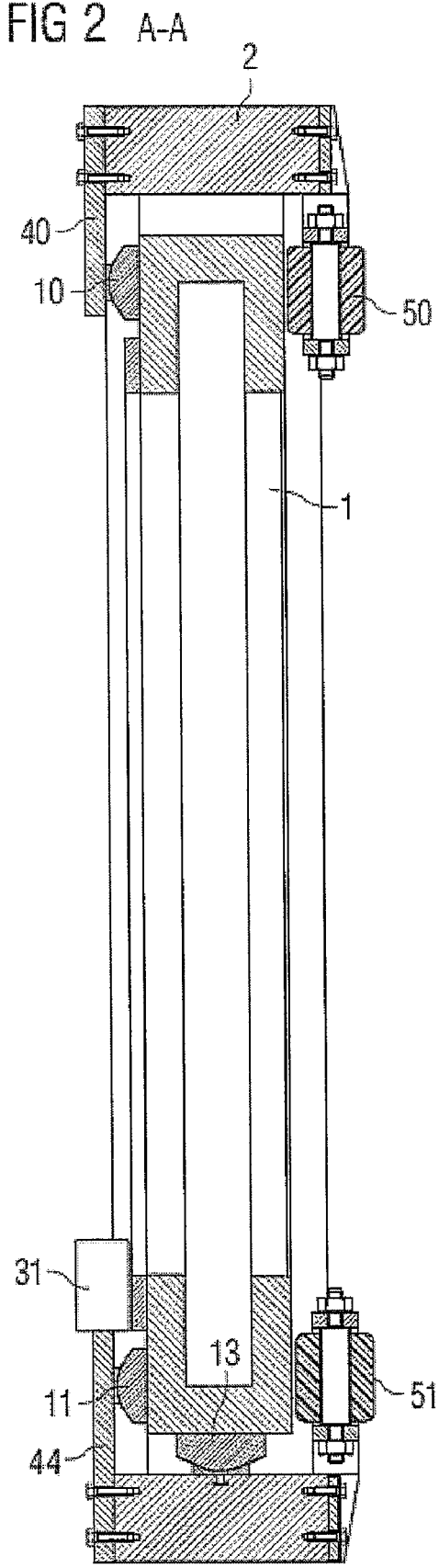
FIG. 2 shows the device of FIG. 1 in a cross-section along the axis A-A.

FIG. 2 shows a section along the axis A-A of FIG. 1. Here the axial air bearings 10 and 11 which are disposed on a front side of the rotor 1 can be discerned particularly well. Furthermore, the motor segment 31 with its support 44 can be discerned. Support rolls 50 and 51 attached to the stator can be discerned on a rear side of the rotor.

Figure 3:
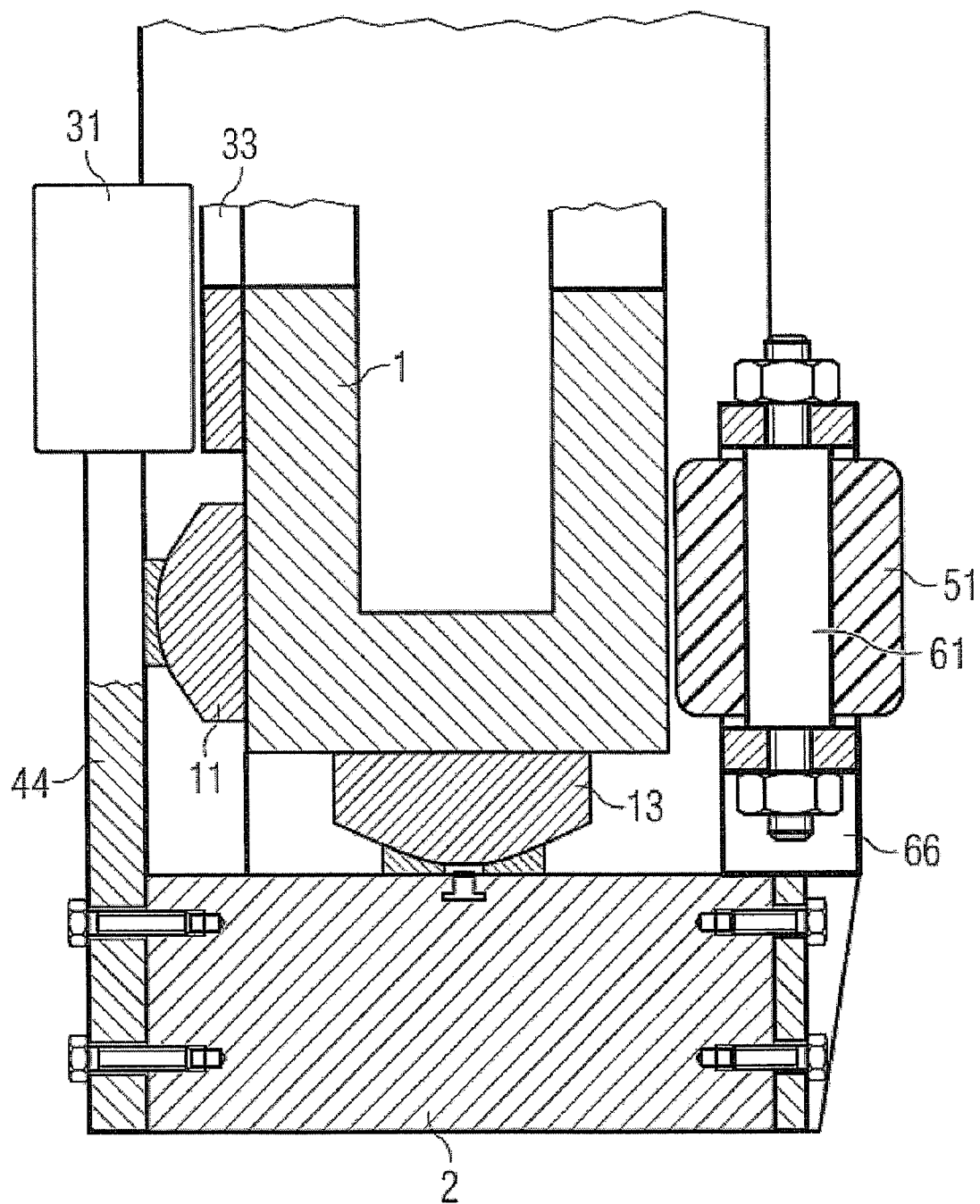
FIG. 3 shows a cut-out portion of a lower part of FIG. 2.

FIG. 3 shows a magnified illustration of a section of the lower part of FIG. 2. Here a holder 66 for the axial support roll 51 which is rotatably supported on a shaft 61 is illustrated. A function of bearing all support rolls can be effected optionally with sliding bearings or ball bearings.

Figure 4:
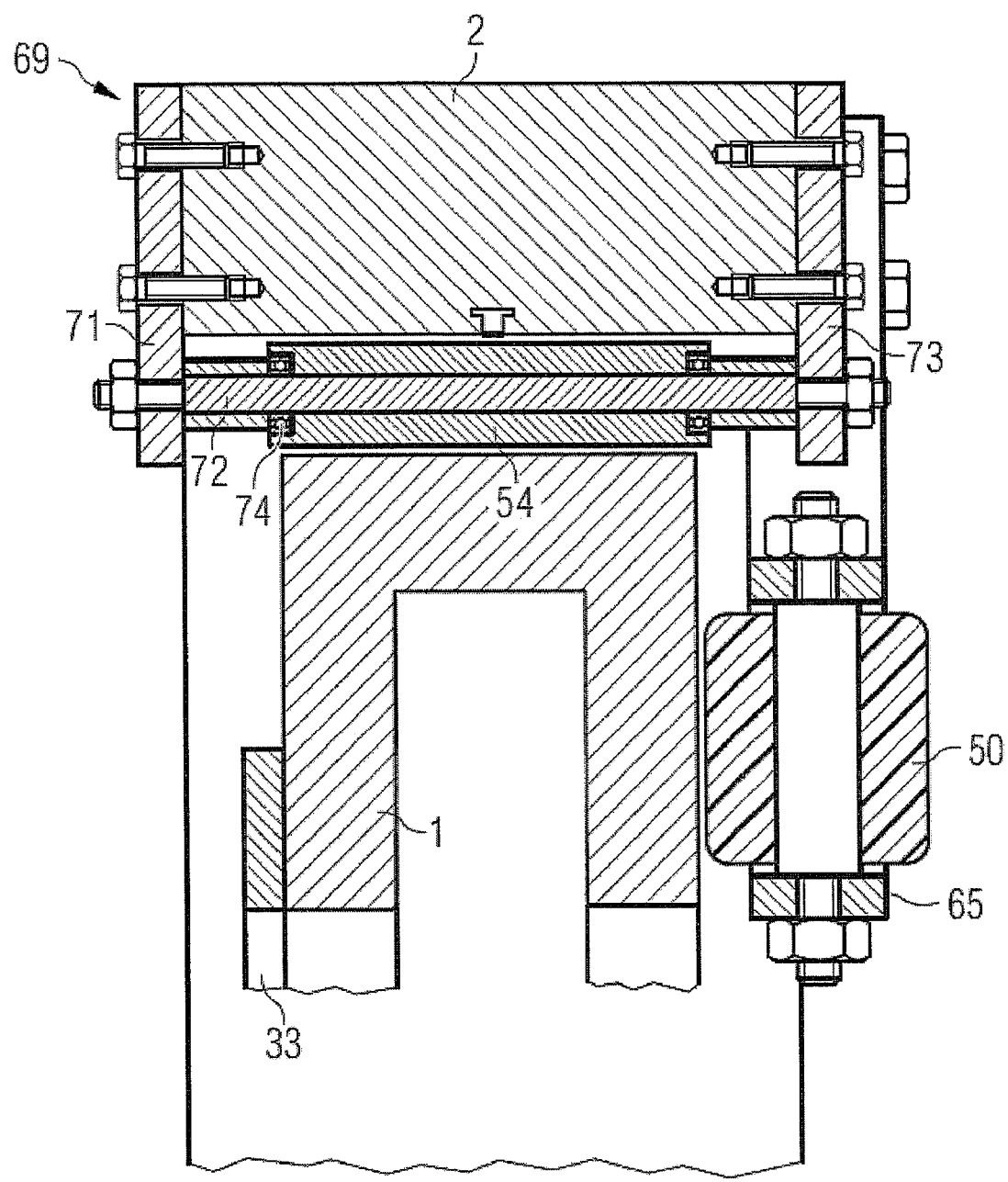
FIG. 4 shows a section of the device of FIG. 1 at a location of the support roll.

FIG. 4 shows a section through the arrangement of FIG. 1 at a location of the radial support roll 54. This support roll is preferably made of a synthetic material. It includes preferably at least one ball bearing 74 and has its axis 72 fixed to the stator 2 via support plates 71 and 73. The entire supporting means for the radial support roll 54 is designated by the reference numeral 69. Furthermore, the support roll 50 together with its holder 65 also can be discerned.

Figure 5:
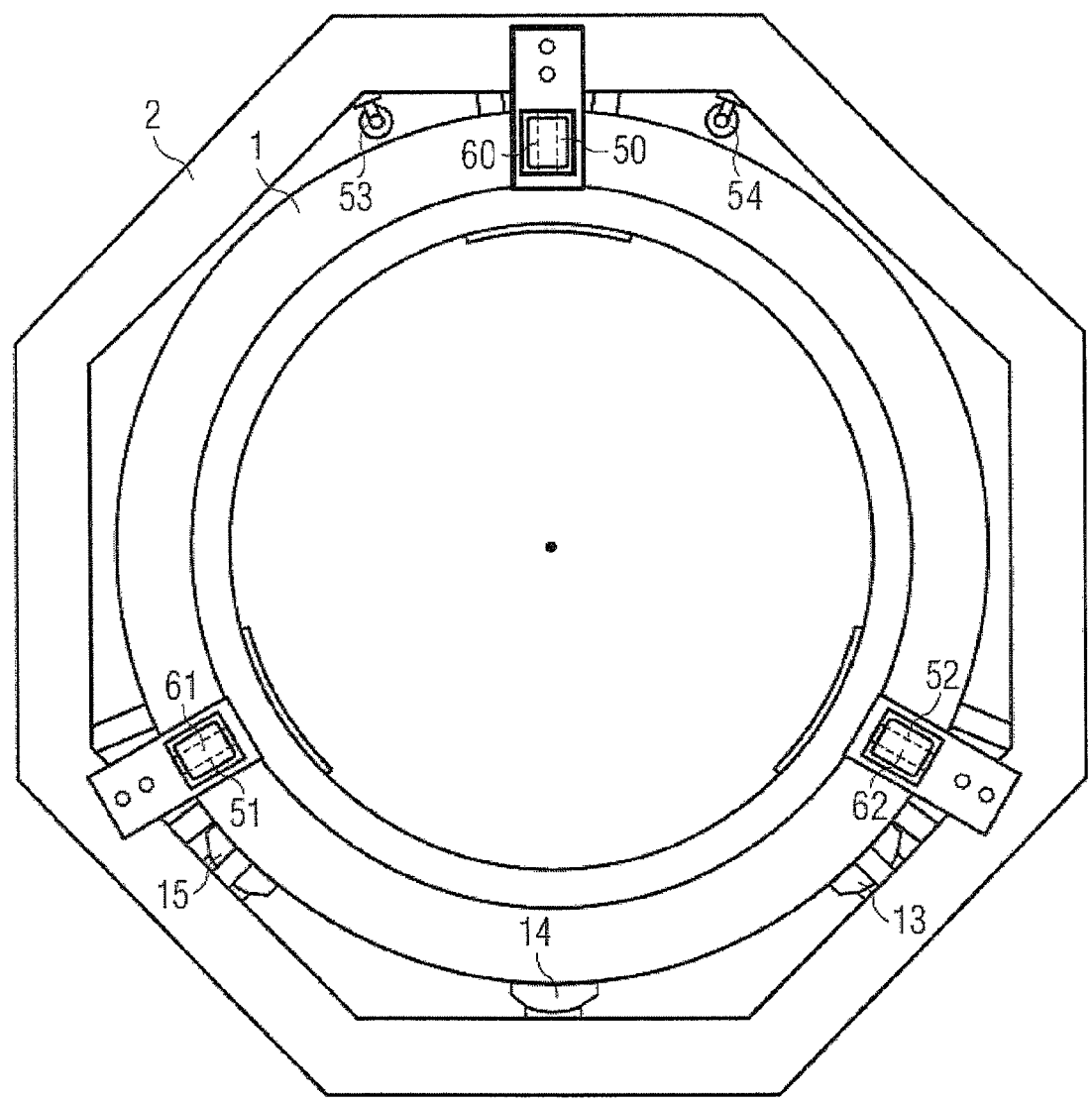
FIG. 5 shows a first device from a rear side.

FIG. 5 shows the device of FIG. 1 from a rear side. Here the axial support rolls 50, 51, 52 in their holders 65, 66, 67 can be clearly discerned.

DETAILED DESCRIPTION OF THE PREFERRED EMBODIMENTS

An embodiment of a device includes a rotor 1 which is supported in a stator 2 to be rotatable around a rotation axis 3. The bearing means includes radial and axial aerostatic bearings. The bearings are each formed of a bearing pad fastened on the stator, and a face of the rotor running thereon. The radial bearing means includes at least one air bearing 13, 14, 15. Preferably two air bearings 13, 15 are provided which preferably are disposed at an angle of 30° to 60°, and most preferably at 45° to the perpendicular to the rotation axis. Especially for use with high loads, another bearing 14 can be provided preferably vertically below the rotation axis. These radial air bearings are disposed below the center of the rotor and carry the weight thereof. Accordingly, a load force on these bearings results from the weight of the rotor. The axial bearing function is effected with the three air bearings 10, 11, and 12 which preferably are disposed at an angle of 120° to each other along the circumference of the rotor. In order to generate the necessary load force on these bearings, contrary to the disclosure of prior art no other set of air bearings is disposed on the other side of the rotor. Rather than this, the force of the motor is used for this.

The motor is a direct drive, which is mounted directly and without further coupling elements such as driving belts and chains on the rotor and stator of the rotatable device. It has a ring-shaped part 33 which is firmly connected to the rotor 1 of the arrangement. At least one motor segment 39, 32, 32 is in engagement with the ring-shaped part 33. As an alternative to this, it is also possible for the ring-shaped part 33 to be connected to the stator, and for at least one motor segment to be connected to the rotor. Preferably, three motor segments are provided which are most preferably distributed uniformly around the circumference of the ring-shaped part at angles of 120° relative to each other. It is of especial advantage for these motor segments to be fastened at the same positions of the stator as the axial air bearings 10, 11, and 12, because thereby force can be directly transmitted from the motor segments into the air bearings. Thus, no transmission of force occurs via the stator of the device. Of course, an arrangement at other positions is also possible. However, basically any other number of motor segments can be used. Alternatively, the motor segments can also cover the entire circumference of the ring-shaped part.

Basically, a motor segment can have a curvature corresponding to the radius of the ring-shaped portion. Similarly, a motor segment also can be straight when the length of the segment is short in comparison with the radius of the ring-shaped part, so that the variation of the distance between a motor segment and the ring-shaped part along the length of the motor segment is still small. This makes it possible to use also motor segments of linear motors.

In the embodiment a load force is exerted by the motor on an air bearing along the axial direction. The load force of the motor arises from a meshing of the magnetic field of the motor segments 30, 31, and 32 with the ring-shaped portion 33.

In order to make possible a reliable generation of load force at least one motor segment is provided to serve exclusively for generating the load force. Optionally, this motor segment may be a coil which, for example, is supplied with a direct current independently of rotation number. However, it would also be possible to generate a synchronous rotary field for moving the device, which field is exclusively aligned for generating a load force and not a torque. As an alternative to this, a motor segment of this kind can include at least one permanent magnet. With use of permanent magnets, a minimum load force can be attained even at a standstill or a current failure.

Advantageously, these permanent magnets are then dimensioned so that a load force is already generated without any current flow in the motor segments, in order to hold the rotor in its position. Thus, the remaining motor segments of the motor need then generate only a smaller load force. The permanent magnets also can be so dimensioned that their load force is adequate optionally for particular operating conditions such as a position of rest, or even for all operating conditions. Thus, the permanent magnets can be dimensioned so that the load force is sufficient for a vertically standing rotor, but that for an operation with a tilted rotor an additional load force of the motor from the fields of the motor segments is necessary.

Preferably the center of gravity of the rotor together with all components fastened thereto is located along an axial direction above the air bearings 13, 14, 15, and more preferably in their middle. This results in a relatively stable position of the arrangement in a position of rest. In an operating condition, as soon as the rotor is set into rotation by the direct drive, the motor generates the necessary load force in order to hold the rotor in a defined position by means of the axial air bearings.

In this case, a particularly good support results when the motor segments which produce the load force are preferably disposed oppositely from the radial bearings with respect to the rotation axis. In a usual case they are therefore disposed above the rotation axis.

Now, because in the arrangement no further air bearings are provided on the side of the rotor opposite to the axial air bearings, the case could arise, for example with the motor switched off and when no load force is generated on an axial air bearing, that the rotor drops away from the axial air bearings along an axial direction and away from the radial air bearings, and thus out of the arrangement. This can lead to a destruction of the entire device. In order to prevent this, at least one axial support roll 50, 51, 52 is furthermore provided. These support rolls are preferably distributed uniformly along the circumference of the rotor. In the case of a support roll, its position on the circumference is preferably on the upper side, and most preferably at the highest point of the arrangement. In the case of three support rolls 50, 51 and 52, these are disposed at angles of 120° with respect to each other. Most preferably they are disposed opposite to the radial air bearings 10, 13, and 15. It is not the purpose of the support rolls to exert the pressure of the rotor on the radial air bearings during normal operation. The support rolls have a pure safety function and are intended to ensure a certain basic bearing-function of the device in the case of a failure of the motor or the air bearings. Preferably ball-bearing-supported synthetic material rolls are provided as the support rolls. The support rolls are preferably mounted on the frame of the stator, so that during normal operation they maintain a distance from the rotor which is large enough so that no contact can occur between the rotor and the support rolls even with maximum tolerances of the axial air bearings. A distance of this kind is preferably of an order of magnitude between 0.5 and 5 mm, and most preferably between 1 and 2 mm.

In another embodiment, additional radial support rolls 53 and 54 are provided which also prevent too large a separation of the rotor from the radial air bearings 13, 14, and 15. This could occur for example with transportable instruments during transport. Similarly to the axial support rolls, these support rolls also are spaced from the rotor so that they cannot contact the rotor during normal operation.

In order to ensure always a defined load force of the rotor on the axial air bearings, a special motor control means 80 is provided. This motor control means drives the motor so that a given bearing load force is always set. For this, preferably the motor current is maintained to be constant independently from the speed of the arrangement. Thus, in particular, a constant motor current must flow through the motor even when the arrangement is at a standstill. 'With this arrangement a distinction must be made between a non-operative state and a standstill of the rotor during which it does not rotate. During a non-operative state the motor is without current, and the air bearings are not supplied with air. The motor rests on the air bearings 13, 14 and 15. This is a stable non-operative state which, as the case may be and according to the actual position of the rotor, is supported also by the axial support rolls 50, 51 and 52. As soon as the device commences operation, the air bearings are first supplied with air so that the rotor is raised from the air bearings. Now the motor can be supplied with current, simultaneously or with a time difference. For this, the motor current is first controlled so that during a standstill of the motor a given force is generated between the rotor and the axial air bearings. If now the motor is to be set into rotation, then the motor is controlled so that it generates a rotary field.

The preferred field of application of the device is in computer tomographs, because here especially high demands are made on speed and tolerances, simultaneously with a very high rotating mass of the rotor. Of course, the arrangement can be used also in other fields of application, such as, for example, in industrial plant construction, in rotary indexing machines, or also in centrifuges.

A regulation of the bearing load force generated by the motor is optionally provided. This can be effected, for example, on the basis of a force measurement of the load force on the axial hydrostatic bearings, or indirectly via the motor current. Similarly, also a path measurement can be made directly with a path sensor, or indirectly for example via the bearing clearance or the air consumption of the bearing, because the bearing load force also affects the bearing gap.

Because of the support rolls, the device has a certain stability under emergency running conditions, so that at least during a failure of the motor the rotor can continue to run to a standstill without any driving power, whilst dissipating its kinetic energy. Substantially more problems arise in an operating condition in which the air bearings or aerostatic bearings can be no longer supplied with air or gas. This can be the case for example with a current failure, or with a failure or a fault of the air supply means such as the compressor. An operating condition of this kind can occur also in a general case with rotatable devices having aerostatic bearing means, as with CT scanners. For a case of this kind, the surfaces of the air bearings must have certain emergency running or sliding characteristics, on the hand, and can be adapted also to absorb the energy of motion, on the other hand, in order to make possible a more rapid braking of the rotor to a standstill. In any case, an abrupt braking of the rotor to a standstill must be avoided, because otherwise the energy of motion to be suddenly converted can lead to massive mechanical deformation or destruction of the device, and also to further damage, for example by scattered parts.

Accordingly, the embodiments disclosed herein improve the emergency running properties of rotatable devices having aerostatic bearing means, such as CT scanners.

An embodiment includes a rotor having a synthetic material surface, with bearing pads of the air bearings comprised, for example, of aluminum or another metal. Thus, owing to the friction during emergency running, the synthetic material can become liquid and thereby dissipate the energy.

Another embodiment includes a rotor of aluminum and air bearing surfaces of sintered graphite. In this case the graphite of the bearing pad surfaces can lubricate the aluminum rotor during emergency running and thereby become worn away. In both of the previously described cases, the energy can be dissipated by mechanical conversion or deformation of the bearing faces during an emergency running of the bearing. This has the consequence that the bearing subsequently must be re-worked or even replaced partially. In this, individual bearing pads or even bearing faces could be replaced selectively.

In another embodiment, at least two separate systems are provided for air supply to the hydrostatic bearings. Advantageously each air supply system includes its own pressure tank, and most advantageously even its own compressor. For example, a plurality of air supply systems could be decoupled by non-return valves and commonly lead into a bearing pad. As an alternative to this, also at least two channel systems for air supply could be provided in individual bearing pads, with each channel system being coupled with its own air supply system. Thus, during a failure of an air supply system, at least a certain minimum air supply into the bearing pad is still ensured.

In addition, a specific safety logic can be applied for control to increase safety. For example, following an actuation of an emergency circuit breaker, the compressor should not be cut-off from current. Furthermore, the motor should be used for active braking of the system in case one or a plurality of the air supply systems fail.

In another embodiment, in the case of an emergency shutdown of the system, a compressor 81 is driven by the kinetic energy of the rotor, in order to ensure sliding characteristics of the bearing means as long as the rotor is still rotating. For this, compressor 81 can be driven optionally directly by the rotor 1. As an alternative to this, however, a generator which feeds compressor 81 can be driven by the rotor 1. A coupling-on of compressor 81 or a generator can be effected here, for example, with a friction wheel or a belt, or also by direct mechanical coupling to the rotor. In case a generator is used for feeding compressor 81, an electronic regulation means for the rotation number or the power supplied by the compressor can be connected into the circuit. In another embodiment, also the motor of the direct drive or at least one motor segment could be operated as a generator for feeding compressor 81. As the required compressor power is of the order of magnitude of one tenth of the driving power for the motor 1, a pressurized air supply down to very low rotor rotation numbers can be ensured. With this arrangement, a need of a pressure tank of extremely large volume can be avoided. If a safety installation of this kind were not provided, then the rotor could continue coasting for up to 20 minutes owing to the extremely low friction of the air bearings. For this entire time of slowing down to a standstill, the necessary quantity of air would have to be stored in a pressure tank. This can now be avoided with the embodiments disclosed herein.

Another improvement of the reliability can be achieved by using a separate motor segment exclusively for feeding the compressor. With this, the motor segment operating as a generator can be operated independently from the drive control means, and can also be used when the drive control means fail.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. Rotatable device comprising:
   a driving motor;
   a rotor;
   a stator, with the rotor supported to be rotatable relative to the stator;
   at least one hydrostatic bearing serving as a radial bearing of the rotor; and
   at least one hydrostatic bearing serving as an axial bearing of the rotor;
   wherein a compressor is provided which is driven by rotational movement of the rotor, and wherein the device is adapted for operation of at least one part of the driving motor as a generator for feeding the compressor when the current supply of the compressor fails.

2. Device according to claim 1, wherein one motor segment of the driving motor is provided exclusively for supplying current to the compressor, and not for driving the rotatable device.

3. Device according to claim 1, wherein at least one axial support roll is provided which, when the motor has attained a given load force, is spaced from a running face of the rotor, and which in the case of too low or of absence of load force prevents a displacement of the rotor away from the axial bearings.

4. Device according to claim 1, wherein the motor has three winding segments.

5. Device according to claim 1, wherein radial support rolls are provided.

* * * * *